(12) United States Patent
Georgescu et al.

(10) Patent No.: US 12,295,774 B2
(45) Date of Patent: May 13, 2025

(54) LARGE VESSEL OCCLUSION DETECTION AND CLASSIFICATION IN MEDICAL IMAGING

(71) Applicant: SIEMENS HEALTHINEERS AG, Forchheim (DE)

(72) Inventors: Bogdan Georgescu, Princeton, NJ (US); Eli Gibson, Plainsboro, NJ (US); Thomas Re, New York, NY (US); Dorin Comaniciu, Princeton, NJ (US)

(73) Assignee: Siemens Healthineers AG, Forchheim (DE)

( * ) Notice: Subject to any disclaimer, the term of this patent is extended or adjusted under 35 U.S.C. 154(b) by 326 days.

(21) Appl. No.: 17/807,772

(22) Filed: Jun. 20, 2022

(65) Prior Publication Data

US 2023/0404512 A1 Dec. 21, 2023

(51) Int. Cl.
*A61B 6/00* (2024.01)
*G06T 7/33* (2017.01)

(52) U.S. Cl.
CPC ............ *A61B 6/5217* (2013.01); *G06T 7/337* (2017.01); *G06T 2207/10081* (2013.01); *G06T 2207/20081* (2013.01); *G06T 2207/20084* (2013.01); *G06T 2207/30016* (2013.01)

(58) Field of Classification Search
CPC .................................. A61B 6/5217; G06T 7/33
See application file for complete search history.

(56) References Cited

U.S. PATENT DOCUMENTS

| | | | |
|---|---|---|---|
| 9,792,531 B2 | 10/2017 | Georgescu et al. | |
| 10,373,313 B2 | 8/2019 | Ghesu et al. | |
| 2014/0107479 A1* | 4/2014 | Klaiman | A61B 6/481 600/431 |
| 2018/0366225 A1* | 12/2018 | Mansi | H04L 67/12 |
| 2020/0394793 A1* | 12/2020 | Namias | G06T 5/30 |
| 2021/0059623 A1* | 3/2021 | Straka | A61B 6/504 |
| 2021/0209757 A1* | 7/2021 | Min | A61B 8/12 |
| 2021/0236080 A1* | 8/2021 | Herrmann | G06T 7/70 |

(Continued)

OTHER PUBLICATIONS

H. Hong et al, "Automatic vessel extraction by patient motion correction and bone removal in brain CT angiography", International Congress Series, vol. 1281, pp. 369-374, 2005 (Year: 2005).*

(Continued)

*Primary Examiner* — Joel Lamprecht
*Assistant Examiner* — Nyrobi Celestine

(57) ABSTRACT

Systems and methods for occlusion detection in medical images are provided. An input medical image of one or more vessels in an anatomical object of a patient is received. One or more anatomical landmarks are identified in the input medical image. A first patch and one or more additional patches are extracted from the input medical image based on the identified one or more anatomical landmarks. The first patch and the one or more additional patches depict different portions of the anatomical object. Features are extracted from the first patch and the one or more additional patches using a machine learning based feature extractor network. An occlusion in the one or more vessels is detected in the first patch based on the extracted features with or without modeling features on a probability distribution function. Results of the detecting are output.

20 Claims, 6 Drawing Sheets

(56) References Cited

U.S. PATENT DOCUMENTS

2021/0374950 A1* 12/2021 Gao ................. G06T 7/70
2022/0125323 A1* 4/2022 Smith ................ A61B 5/1102

OTHER PUBLICATIONS

X. Wang et al, "Skeleton-based cerebrovascular quantitative analysis", BMC Medical Imaging, vol. 16, No. 68, pp. 1-15, 2016 (Year: 2016).*
M. Zreik et al, "A Recurrent CNN for Automatic Detection and Classification of Coronary Artery Plaque and Stenosis in Coronary CT Angiography", IEEE Transactions on Medical Imaging, vol. 38, No. 7, Jul. 2019 (Year: 2019).*
G. Chen et al, "Automated computer assisted detection system for cerebral aneurysms in time of flight magnetic resonance angiography using fully convolutional network", BioMedical Engineering OnLine, vol. 19, No. 38, pp. 1-10, 2020 (Year: 2020).*
J. Soun et al, "Artificial Intelligence and Acute Stroke Imaging", American Journal of Neuroradiology, vol. 42, No. 1, pp. 2-11, Jan. 2021 (Year: 2021).*
R. Rava et al, "Validation of an artificial intelligence-driven large vessel occlusion detection algorithm for acute ischemic stroke patients", The Neuroradiology Journal, vol. 34, No. 5, pp. 408-417, 2021 (Year: 2021).*
A. Yahav-Dovrat et al, "Evaluation of Artificial Intelligence-Powered Identification of Large-Vessel Occlusions in a Comprehensive Stroke Center", American Journal of Neuroradiology, vol. 42, pp. 247-254, Feb. 2021 (Year: 2021).*
P. Cimflova et al, "Validation of a machine learning software tool for automated large vessel occlusion detection in patients with suspected acute stroke", Neuroradiology, vol. 64, pp. 2245-2255, May 2022 (Year: 2022).*
Y. Wang et al, "A deep symmetry convnet for stroke lesion segmentation", 2016 IEEE International Conference on Image Processing (ICIP), pp. 111-115, 2016 (Year: 2016).*
G. Praveen et al, "Ischemic stroke lesion segmentation using stacked sparse autoencoder", Computers in Biology and Medicine, vol. 99, pp. 38-52, May 2018 (Year: 2018).*
Y. Wang et al, "A 3D Cross-Hemisphere Neighborhood Difference Convnet for Chronic Stroke Lesion Segmentation", 2019 IEEE International Conference on Image Processing (ICIP), pp. 1545-1549, 2019 (Year: 2019).*
A. Barman et al, "Determining Ischemic Stroke From CT-Angiography Imaging Using Symmetry-Sensitive Convolutional Networks", 2019 IEEE International Symposium on Biomedical Imaging, pp. 1873-1877, Apr. 2019 (Year: 2019).*
You et al, "3D dissimilar-siamese-u-net for hyperdense Middle cerebral artery sign segmentation", Computerized Medical Imaging and Graphics, vol. 90, pp. 1-13, 2021 (Year: 2021).*
Malhotra et al, "Ischemic strokes due to large-vessel occlusions contribute disproportionately to stroke-related dependence and death: a review", Frontiers Neurology, 2017, pp. 1-6.
Amukotuwa et al, "Automated Detection of Intracranial Large Vessel Occlusions on Computed Tomography Angiography: A Single Center Experience", Stroke, 2019, vol. 50, pp. 2790-2798.
Murray et al, "Artificial intelligence to diagnose ischemic stroke and identify large vessel occlusions: a systematic review", J Neurointerv Surg, 2019, pp. 1-10.
Ghesu et al, "Multi-Scale Deep Reinforcement Learning for Real-Time 3D-Landmark Detection in CT Scans", IEEE Transactions on Pattern Analysis and Machine Intelligence, 2017, pp. 1-14.
Yang et al, "Automatic liver segmentation using an adversarial image-to-image network", International Conference on Medical Image Computing and Computer-Assisted Intervention, Springer. pp. 1-9.
U.S. Appl. No. 17/449,263, filed Sep. 29, 2021, 43 pgs.
U.S. Appl. No. 17/449,298, filed Sep. 29, 2021, 40 pgs.
Extended European Search Report (EESR) mailed Dec. 7, 2023 in corresponding European Patent Application No. 23180035.0.
Barman Arko et al: "Determining Ischemic Stroke From CT-Angiography Imaging Using Symmetry-Sensitive Convolutional Networks", 2019 IEEE 16th International Symposium on Biomedical Imaging (ISBI 2019), IEEE, Apr. 8, 2019 (Apr. 8, 2019), pp. 1873-1877.
You Jia et al: "3D dissimilar-siamese-u-net for hyperdense Middle cerebral artery sign segmentation", Computerized Medical Imaging and Graphics, Pergamon Press, New York, NY, US, vol. 90, Mar. 14, 2021 (Mar. 14, 2021).
Wang Yan-Ran et al: "A 3D Cross-Hemisphere Neighborhood Difference Convnet for Chronic Stroke Lesion Segmentation" 2019 IEEE International Conference On Image Processing (ICIP), IEEE, Sep. 22, 2019 (Sep. 22, 2019), pp. 1545-1549.

* cited by examiner

```
┌─────────────────────────────────────────────────────────┐
│ Receive an input medical image of one or more vessels  │
│ in an anatomical object of a patient                    │
│ 202                                                     │
└─────────────────────────────────────────────────────────┘
                            │
                            ▼
┌─────────────────────────────────────────────────────────┐
│ Remove bone from the input medical image                │
│ 204                                                     │
└─────────────────────────────────────────────────────────┘
                            │
                            ▼
┌─────────────────────────────────────────────────────────┐
│ Identify one or more anatomical landmarks in the input  │
│ medical image                                           │
│ 206                                                     │
└─────────────────────────────────────────────────────────┘
                            │
                            ▼
┌─────────────────────────────────────────────────────────┐
│ Extract a first patch and one or more additional        │
│ patches from the bone-removed input medical image       │
│ based on the identified one or more anatomical          │
│ landmarks, the first patch and the one or more          │
│ additional patches depicting different portions of the  │
│ anatomical object                                       │
│ 208                                                     │
└─────────────────────────────────────────────────────────┘
                            │
                            ▼
┌─────────────────────────────────────────────────────────┐
│ Extract features from the first patch and the one or    │
│ more additional patches using a machine learning based  │
│ feature extractor network                               │
│ 210                                                     │
└─────────────────────────────────────────────────────────┘
                            │
                            ▼
┌─────────────────────────────────────────────────────────┐
│ Detect an occlusion in the one or more vessels in the   │
│ first patch based on the extracted features             │
│ 212                                                     │
└─────────────────────────────────────────────────────────┘
                            │
                            ▼
┌─────────────────────────────────────────────────────────┐
│ Output results of the detecting                         │
│ 214                                                     │
└─────────────────────────────────────────────────────────┘
```

|  | AUC | Sens | Spec |
|---|---|---|---|
| Global | 0.96 | 0.92 | 0.92 |
| ICA | 0.99 | 1.00 | 0.90 |
| MCA M1 | 0.97 | 0.96 | 0.88 |
| MCA M2 | 0.96 | 0.92 | 0.94 |

LARGE VESSEL OCCLUSION DETECTION AND CLASSIFICATION IN MEDICAL IMAGING

TECHNICAL FIELD

The present invention relates generally to medical image analysis, and in particular to large vessel occlusion (LVO) detection and classification in medical imaging.

BACKGROUND

A stroke occurs when the blood supply to the brain is interrupted or reduced. Strokes can be classified as ischemic strokes caused by an interruption of the blood supply to the brain or hemorrhagic strokes resulting from a rupturing of a blood vessel. In the current stroke protocol, if a stroke is ischemic, a computed tomography angiography (CTA) scan is performed to determine whether there is a large vessel occlusion (LVO) in the main cerebral arteries. A mechanical thrombectomy can then be performed to remove the LVO.

Various conventional artificial intelligence (AI) based approaches for LVO detection have been proposed. However, such conventional AI based approaches have reduced robustness and performance in the presence of signal dropout, noise, vessel tortuosity, calcification, and proximity to bone or bifurcations.

BRIEF SUMMARY OF THE INVENTION

In accordance with one or more embodiments, systems and methods for occlusion detection in medical images are provided. An input medical image of one or more vessels in an anatomical object of a patient is received. One or more anatomical landmarks are identified in the input medical image. A first patch and one or more additional patches are extracted from the input medical image based on the identified one or more anatomical landmarks. The first patch and the one or more additional patches depict different portions of the anatomical object. Features are extracted from the first patch and the one or more additional patches using a machine learning based feature extractor network. An occlusion in the one or more vessels is detected in the first patch based on the extracted features. Results of the detecting are output.

In one embodiment, bone is removed from the input medical image. The first patch and the one or more additional patches are extracted from the bone-removed input medical image.

In one embodiment, the features are extracted from the first patch and the one or more additional patches by receiving the first patch via a first input channel of the machine learning based feature extractor network and the one or more additional patches via a respective one of one or more additional input channels of the machine learning based feature extractor network and extracting 1) features from the first patch and 2) features comparing the first patch with the one or more additional patches. The occlusion in the one or more vessels is detected in the first patch.

In one embodiment, the first patch and the one or more additional patches are cropped centered around the one or more anatomical landmarks.

In one embodiment, the occlusion in the one or more vessels is detected in the first patch using a probability distribution function (PDF) model fitted on features extracted by a neural network. The PDF model may be learned using a Gaussian Process model.

In one embodiment, a middle cerebral artery (MCA) bifurcation is identified in the input medical image. The first patch is cropped centered around the MCA bifurcation. The occlusion is detected as being in one of an internal carotid artery (ICA), an MCA M1 segment, or MCA M2 segment.

In one embodiment, at least one probability map of vessel presence is generated for at least one of the first patch or the one or more additional patches. Features are extracted from the at least one probability map using the machine learning based feature extractor network.

In one embodiment, the anatomical object comprises a brain of the patient and the different portions comprise a left side of the brain and a right side of the brain.

These and other advantages of the invention will be apparent to those of ordinary skill in the art by reference to the following detailed description and the accompanying drawings.

BRIEF DESCRIPTION OF THE DRAWINGS

FIG. 2 shows a method detecting an occlusion in one or more vessels of an anatomical object of a patient, in accordance with one or more embodiments;

FIG. 3 shows a table of performance of embodiments described herein during an experimental validation;

DETAILED DESCRIPTION

The present invention generally relates to methods and systems for large vessel occlusion (LVO) detection and classification in medical images. Embodiments of the present invention are described herein to give a visual understanding of such methods and systems. A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, is to be understood that embodiments of the present invention may be performed within a computer system using data stored within the computer system.

Embodiments described herein provide for LVO detection and classification in an input medical image of vessels in a brain of a patient. In one embodiment, features are extracted from a patch depicting a left side of the brain and from a patch depicting a right side of the brain and an occlusion in the vessels is detected based on the extracted features. Advantageously, embodiments described herein provide for LVO detection and classification with increased robustness and performance in the presence of signal dropout, noise, vessel tortuosity, calcification, and proximity to bone or bifurcations as compared to conventional approaches. Such increased robustness and performance are a result of, for example, the patches being extracted from an input medical image based on anatomical landmarks, allowing both absolute as well as differential distributional features to be extracted and used for occlusion detection. In addition, by applying an output model of a probability distribution function based on a Gaussian Process allows for increased confidence decisions. Further, embodiments described herein enable increased automation and trust of deployed systems by reducing the number of errors in semantic image analysis. In one example, embodiments described herein can enable full automation of the entire stroke management workflow on a scanner or edge computer with faster treatment of patients and applications to automatic triage or intervention planning.

Figure 1:
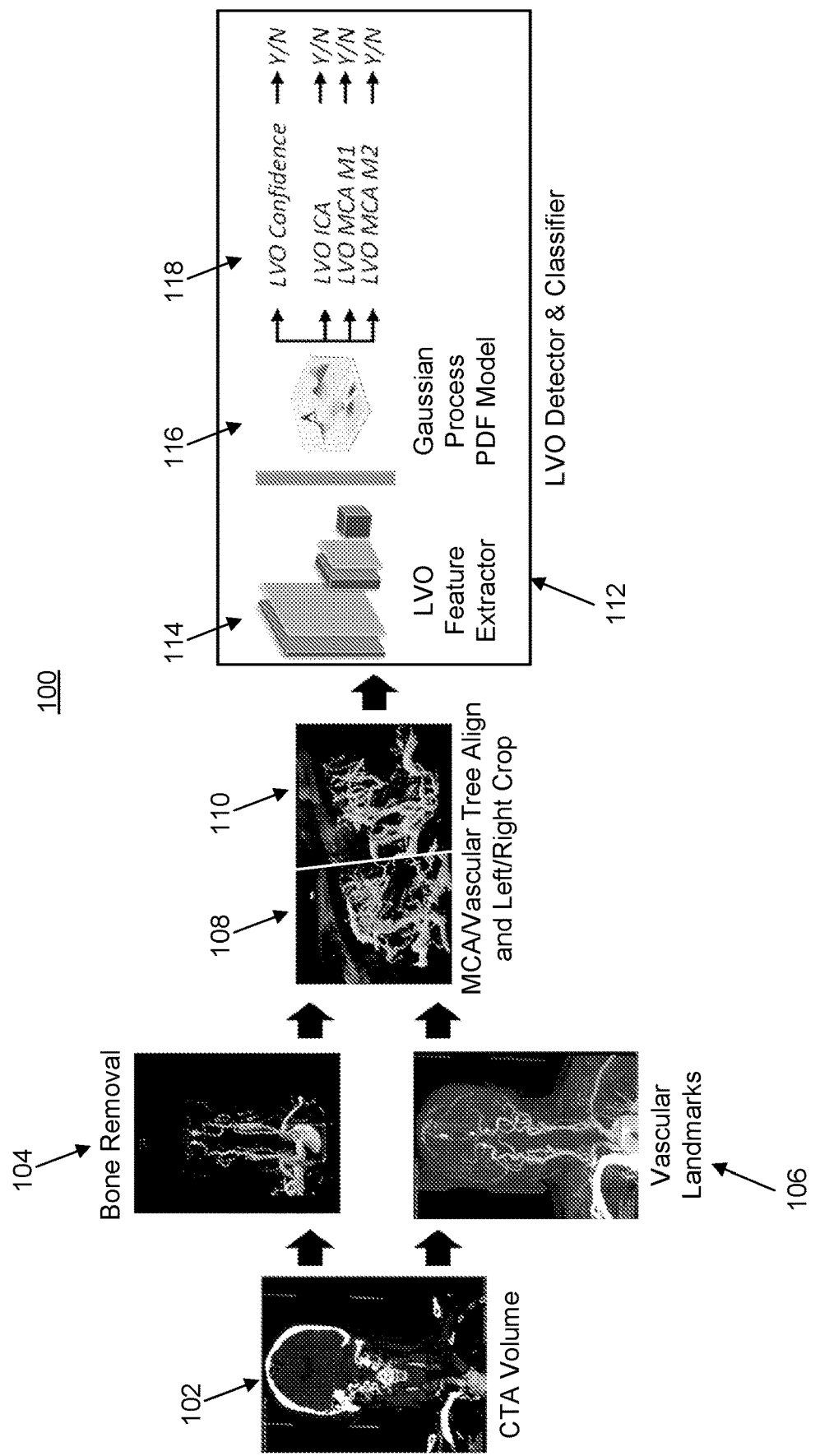
FIG. 1 shows a workflow for automatically detecting an occlusion in one or more vessels of a brain of a patient, in accordance with one or more embodiments.

FIG. 1 shows a workflow 100 for automatically detecting an occlusion in one or more vessels of a brain of a patient, in accordance with one or more embodiments. FIG. 2 shows a method 200 for detecting an occlusion in one or more vessels of an anatomical object of a patient, in accordance with one or more embodiments. FIG. 1 and FIG. 2 will be described together. The steps of method 200 may be performed by one or more suitable computing devices, such as, e.g., computer 602 of FIG. 6.

At step 202 of FIG. 2, an input medical image of one or more vessels in an anatomical object of a patient is received. In one embodiment, the anatomical object is a brain of the patient. However, the anatomical object may be any other suitable anatomical object of interest of the patient, such as, e.g., the lungs.

In one embodiment, the input medical image is a computed tomography (CT) image acquired during a CT angiography (CTA). For example, as shown in workflow 100 of FIG. 1, the input medical image is CTA volume 102. However, the input medical image may be of any other suitable modality, such as, e.g., magnetic resonance imaging (MRI), ultrasound (US), x-ray, or any other medical imaging modality or combinations of medical imaging modalities. The input medical image may be a 2D (two dimensional) image or a 3D (three dimensional) volume, and may comprise a single input medical image or a plurality of input medical images. The input medical image may be received directly from an image acquisition device, such as, e.g., a CT scanner, as the input medical image is acquired, or can be received by loading a previously acquired medical image from a storage or memory of a computer system or receiving medical images that have been transmitted from a remote computer system.

At step 204 of FIG. 2, bone is removed from the input medical image. In one example, as shown in workflow 100 of FIG. 1, bone is removed from CTA volume 102 to generate a bone-removed input medical image 104. In one embodiment, the bone is removed from the input medical image using a machine learning based bone removal network, such as, e.g., a deep-learning based image-to-image (I2I) model. However, the bone may be removed from the input medical image using any other suitable approach.

At step 206 of FIG. 2, one or more anatomical landmarks in the input medical image are identified. In one embodiment, the anatomical landmarks may be vascular landmarks of the vessels. For example, as shown in workflow 100 of FIG. 1, vascular landmarks 106 are identified in CTA volume 102. In one example, the vascular landmarks include the middle cerebral artery (MCA) bifurcation or the basilar artery. Other exemplary vascular landmarks include the brachiocephalic artery, the left common carotid artery, the left subclavian, the left subclavian and vertebralis, the right subclavian and vertebralis branch, the left vertebral artery (C3, C5), the right vertebral artery (C3, C5), the left carotid bifurcation, the right carotid bifurcation, the right carotid enter skull, the left carotid enter skull, the vertebral artery merge to basilar artery, the left intracranial, the right intracranial, the left carotid frontal, the right carotid front, the basilar artery branch, and the carotid artery merge. However, the anatomical landmarks may be any other suitable anatomical landmarks in the input medical image.

In one embodiment, the anatomical landmarks are identified using a machine learning based detection network, such as, e.g., a multi-scale reinforcement learning based model. For example, the anatomical landmarks may be identified by first generating a vessel tree of the one or more vessels and identifying or indexing the anatomical landmarks on the vessel tree using the multi-scale reinforcement learning based model. However, the anatomical landmarks may be identified using any other suitable approach.

At step 208 of FIG. 2, a first patch and one or more additional patches are extracted from the bone-removed input medical image based on the identified one or more anatomical landmarks. For example, as shown in workflow 100 of FIG. 1, first patch 108 and second patch 110 are extracted from bone-removed input medical image 104 based on vascular landmarks 106. The first patch and the one or more additional patches depict different portions of the anatomical object. In one embodiment, where the anatomical object is the brain of the patient, the first patch 108 depicts a left side of the brain and the second patch 110 depicts a right side of the brain (or vice versa).

In one embodiment, the first patch and the one or more additional patches are extracted from the bone-removed input medical image by cropping the bone-removed input medical image such that the patches are aligned to (e.g., centered around) the anatomical landmarks. The first patch and the one or more additional patches may be of any suitable dimension. In one embodiment, the first patch and the one or more additional patches are of predetermined dimensions.

At step 210 of FIG. 2, features are extracted from the first patch and the one or more additional patches using a machine learning based feature extractor network. The machine learning based feature extractor network receives the first patch and the one or more additional patches as input and generates the features as output. The first patch is received via a first input channel of the machine learning based feature extractor network and the one or more additional patches are received via a respective one of one or more additional input channels of the machine learning based feature extractor network. The machine learning based feature extractor network may be any suitable machine learning based network, such as, e.g., networks based on convolutional deep neural networks or vision transformer architectures.

In one example, as shown in workflow 100 of FIG. 1, features are extracted from first patch 108 and second patch 110 using LVO feature extractor 114 of LVO detector and classifier 112. As shown in workflow 100 of FIG. 1, LVO feature extractor 114 receives as input first patch 108 and second patch 110 as separate input channels and generates the features as output. In one embodiment, a first input channel receives first patch 108 and a second input channel receives second patch 110. The features are latent features extracted from first patch 108 and second patch 110. The features comprise vessel density features specific to the patch received via the first input channel (e.g., first patch 108 in this embodiment), as well as differential features comparing the first patch with each of the one or more additional patches (e.g., first patch 108 and second patch 110 to compare the first portion with the second portion of the anatomical object respectively). The extraction of the differential features is enabled by the input of both first patch 108 and second patch 110 into LVO feature extractor 114.

At step 212 of FIG. 2, an occlusion (e.g., an LVO) in the one or more vessels is detected in the first patch based on the extracted features. In one embodiment, an output model is trained to detect the occlusion depicted in the patch received via the first input channel of the feature extractor network. In one embodiment, the output model is a probability distribution function (PDF) model fitted on features extracted by, e.g., a neural network. The PDF model is learned using a Gaussian Process model. However, the output model may be any other suitable model for detecting an occlusion based on the extracted features. For example, the output model may be aa machine learning based classifier network such as, e.g., a deep learning based multi-label classifier or a model based on other probability distributions (Gaussian Mixtures or Kernel Density Estimates).

In one example, as shown in workflow 100 of FIG. 1, Gaussian Process PDF Model 116 of LVO detector and classifier 112 receives features extracted by LVO feature extractor 114 as input and generates results 118 as output. Results 118 are results of the detection of an occlusion in the patch received via the first input channel of LVO feature extractor 114 (e.g., first patch 108 in this embodiment). In one example, as shown in workflow 100 of FIG. 1, results 118 comprise numerical values (e.g., between 0 and 1) indicating an LVO confidence (representing the confidence of an LVO in the vessels depicted in the patch receives via the first input channel), as well as a confidence that the LVO is part of specific portions of the vessels, such as, e.g., the internal carotid artery (ICA), middle cerebral artery (MCA) at the M1 level, and MCA at the M2 level. A confidence for other vessels (e.g., corresponding to anterior or posterior circulation) may also be included. The values may be compared with one or more thresholds (e.g., 0.5) to generate a classification (e.g., a binary classification of yes or no). In one embodiment, Gaussian Process PDF Model 116 is trained on the feature distribution extracted by LVO feature extractor 114, which allows for the consideration of uncertainty in the input data or the model for additional tuning in triage applications.

In one embodiment, where the one or more identified anatomical landmarks comprises an MCA bifurcation and where the first patch is cropped centered around the MCA bifurcation, the occlusion is detected as being on one of an internal carotid artery (ICA), an MCA M1 segment (i.e., the sphenoidal segment), or MCA M2 segment (i.e., the insular segment). A similar process may be applied for the basilar artery.

At step 214 of FIG. 2, the results of the detecting are output. For example, the results of the detecting can be output by displaying the results on a display device of a computer system, storing the results on a memory or storage of a computer system, or by transmitting the results to a remote computer system. In one embodiment, the results of the detecting may be used for worklist prioritization or automated notification when deployed on a scanner (e.g., CT scanner) or in a standalone or cloud process system, or may be used to automate intervention planning, such as, e.g., for a mechanical thrombectomy.

In one embodiment, at step 210 of FIG. 2, the feature extractor network additionally or alternatively receives at least one probability map of vessel presence in at least one of the first patch or the one or more additional patches as input and extracts the features from the probability maps. The probability maps may be generated using a vesselness classifier or filter that receives the first patch and/or the one or more additional patches as input and generates respective probability maps as output.

In one embodiment, at step 208 of FIG. 2, the first patch and the one or more additional patches may be extracted from the input medical image at different regions of the vessel tree, such as, e.g., posterior circulation (focused on the basilar artery) or at the carotid bifurcation to external carotid artery.

Embodiments described herein were experimentally validated on a database of 2647 CTA volumes. FIG. 3 shows a table 300 of performance of embodiments described herein during an experimental validation. As shown in table 300, the experiments resulted in an overall sensitivity (Sens) of 92%, a specificity (Spec) of 92%, and an area under curve (AUC) of 0.96 for a hold-out test set including 60 patients. Table 300 also shows the sensitivity, specificity, and AUC of LVO detections in the ICA, MCA M1, and MCA M2.

Embodiments described herein are described with respect to the claimed systems as well as with respect to the claimed methods. Features, advantages or alternative embodiments herein can be assigned to the other claimed objects and vice versa. In other words, claims for the systems can be improved with features described or claimed in the context of the methods. In this case, the functional features of the method are embodied by objective units of the providing system.

Furthermore, certain embodiments described herein are described with respect to methods and systems utilizing trained machine learning based networks (or models), as well as with respect to methods and systems for training machine learning based networks. Features, advantages or alternative embodiments herein can be assigned to the other claimed objects and vice versa. In other words, claims for methods and systems for training a machine learning based network can be improved with features described or claimed in context of the methods and systems for utilizing a trained machine learning based network, and vice versa.

In particular, the trained machine learning based networks applied in embodiments described herein can be adapted by the methods and systems for training the machine learning based networks. Furthermore, the input data of the trained machine learning based network can comprise advantageous features and embodiments of the training input data, and vice versa. Furthermore, the output data of the trained machine learning based network can comprise advantageous features and embodiments of the output training data, and vice versa.

In general, a trained machine learning based network mimics cognitive functions that humans associate with other human minds. In particular, by training based on training data, the trained machine learning based network is able to adapt to new circumstances and to detect and extrapolate patterns.

In general, parameters of a machine learning based network can be adapted by means of training. In particular, supervised training, semi-supervised training, unsupervised training, reinforcement learning and/or active learning can be used. Furthermore, representation learning (an alternative term is "feature learning") can be used. In particular, the parameters of the trained machine learning based network can be adapted iteratively by several steps of training.

In particular, a trained machine learning based network can comprise a neural network, a support vector machine, a decision tree, and/or a Bayesian network, and/or the trained machine learning based network can be based on k-means clustering, Q-learning, genetic algorithms, and/or association rules. In particular, a neural network can be a deep neural network, a convolutional neural network, or a convolutional deep neural network. Furthermore, a neural network can be an adversarial network, a deep adversarial network and/or a generative adversarial network.

Figure 4:
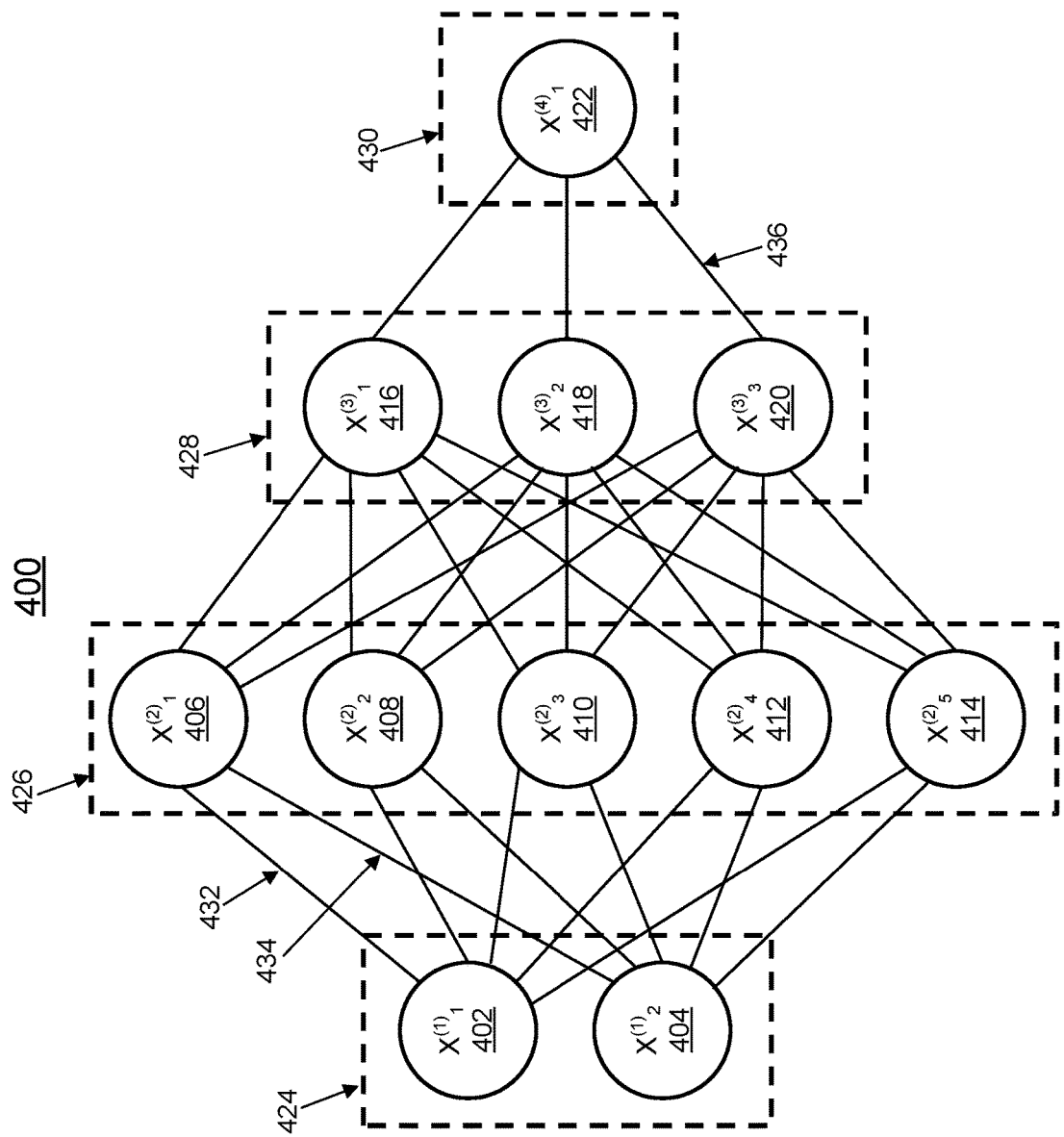
FIG. 4 shows an exemplary artificial neural network that may be used to implement one or more embodiments.

FIG. 4 shows an embodiment of an artificial neural network 400, in accordance with one or more embodiments. Alternative terms for "artificial neural network" are "neural network", "artificial neural net" or "neural net". Machine learning networks described herein, such as, e.g., the LVO feature extractor 114 of FIG. 1, the machine learning based bone removal network utilized at step 204 of FIG. 2, the machine learning based detection network utilized at step 206 of FIG. 2, the machine learning based feature extractor network utilized at step 210 of FIG. 2, the machine learning based classifier network utilized at step 212 of FIG. 2, may be implemented using artificial neural network 400.

The artificial neural network 400 comprises nodes 402-422 and edges 432, 434, . . . , 436, wherein each edge 432, 434, . . . , 436 is a directed connection from a first node 402-422 to a second node 402-422. In general, the first node 402-422 and the second node 402-422 are different nodes 402-422, it is also possible that the first node 402-422 and the second node 402-422 are identical. For example, in FIG. 4, the edge 432 is a directed connection from the node 402 to the node 406, and the edge 434 is a directed connection from the node 404 to the node 406. An edge 432, 434, . . . , 436 from a first node 402-422 to a second node 402-422 is also denoted as "ingoing edge" for the second node 402-422 and as "outgoing edge" for the first node 402-422.

In this embodiment, the nodes 402-422 of the artificial neural network 400 can be arranged in layers 424-430, wherein the layers can comprise an intrinsic order introduced by the edges 432, 434, . . . , 436 between the nodes 402-422. In particular, edges 432, 434, . . . , 436 can exist only between neighboring layers of nodes. In the embodiment shown in FIG. 4, there is an input layer 424 comprising only nodes 402 and 404 without an incoming edge, an output layer 430 comprising only node 422 without outgoing edges, and hidden layers 426, 428 in-between the input layer 424 and the output layer 430. In general, the number of hidden layers 426, 428 can be chosen arbitrarily. The number of nodes 402 and 404 within the input layer 424 usually relates to the number of input values of the neural network 400, and the number of nodes 422 within the output layer 430 usually relates to the number of output values of the neural network 400.

In particular, a (real) number can be assigned as a value to every node 402-422 of the neural network 400. Here, $x^{(n)}_i$ denotes the value of the i-th node 402-422 of the n-th layer 424-430. The values of the nodes 402-422 of the input layer 424 are equivalent to the input values of the neural network 400, the value of the node 422 of the output layer 430 is equivalent to the output value of the neural network 400. Furthermore, each edge 432, 434, . . . , 436 can comprise a weight being a real number, in particular, the weight is a real number within the interval [−1, 1] or within the interval [0, 1]. Here, $w^{(m,n)}_{i,j}$ denotes the weight of the edge between the i-th node 402-422 of the m-th layer 424-430 and the j-th node 402-422 of the n-th layer 424-430. Furthermore, the abbreviation $w^{(n)}_{i,j}$ is defined for the weight $w^{(n,n+1)}_{i,j}$.

In particular, to calculate the output values of the neural network 400, the input values are propagated through the neural network. In particular, the values of the nodes 402-422 of the (n+1)-th layer 424-430 can be calculated based on the values of the nodes 402-422 of the n-th layer 424-430 by $$x^{(n+1)}_j = f\left(\sum_i x^{(n)}_i \cdot w^{(n)}_{i,j}\right).$$

Herein, the function f is a transfer function (another term is "activation function"). Known transfer functions are step functions, sigmoid function (e.g. the logistic function, the generalized logistic function, the hyperbolic tangent, the Arctangent function, the error function, the smoothstep function) or rectifier functions. The transfer function is mainly used for normalization purposes.

In particular, the values are propagated layer-wise through the neural network, wherein values of the input layer 424 are given by the input of the neural network 400, wherein values of the first hidden layer 426 can be calculated based on the values of the input layer 424 of the neural network, wherein values of the second hidden layer 428 can be calculated based in the values of the first hidden layer 426, etc.

In order to set the values $w^{(m,n)}_{i,j}$ for the edges, the neural network 400 has to be trained using training data. In particular, training data comprises training input data and training output data (denoted as $t_i$). For a training step, the neural network 400 is applied to the training input data to generate calculated output data. In particular, the training data and the calculated output data comprise a number of values, said number being equal with the number of nodes of the output layer.

In particular, a comparison between the calculated output data and the training data is used to recursively adapt the weights within the neural network 400 (backpropagation algorithm). In particular, the weights are changed according to $$w'^{(n)}_{i,j} = w^{(n)}_{i,j} - \gamma \cdot \delta^{(n)}_j \cdot x^{(n)}_i$$

wherein $\gamma$ is a learning rate, and the numbers $\delta^{(n)}_j$ can be recursively calculated as $$\delta^{(n)}_j = \left(\sum_k \delta^{(n+1)}_k \cdot w^{(n+1)}_{j,k}\right) \cdot f'\left(\sum_i x^{(n)}_i \cdot w^{(n)}_{i,j}\right)$$

based on $\delta^{(n+1)}_j$, if the (n+1)-th layer is not the output layer, and $$\delta^{(n)}_j = \left(x^{(n+1)}_k - t^{(n+1)}_j\right) \cdot f'\left(\sum_i x^{(n)}_i \cdot w^{(n)}_{i,j}\right)$$

if the (n+1)-th layer is the output layer 430, wherein f' is the first derivative of the activation function, and $y^{(n+1)}_j$ is the comparison training value for the j-th node of the output layer 430.

Figure 5:
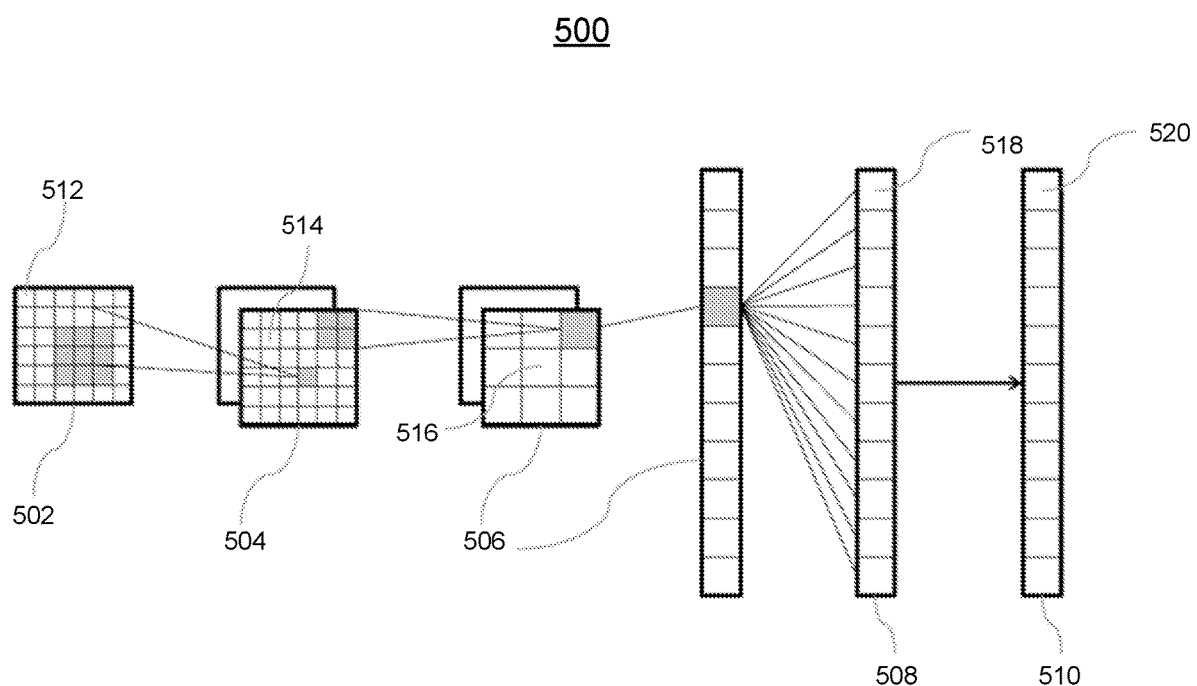
FIG. 5 shows a convolutional neural network that may be used to implement one or more embodiments.

FIG. 5 shows a convolutional neural network 500, in accordance with one or more embodiments. Machine learning networks described herein, such as, e.g., the LVO feature extractor 114 of FIG. 1, the machine learning based bone removal network utilized at step 204 of FIG. 2, the machine learning based detection network utilized at step 206 of FIG. 2, the machine learning based feature extractor network utilized at step 210 of FIG. 2, the machine learning based classifier network utilized at step 212 of FIG. 2, may be implemented using convolutional neural network 500.

In the embodiment shown in FIG. 5, the convolutional neural network comprises 500 an input layer 502, a convolutional layer 504, a pooling layer 506, a fully connected layer 508, and an output layer 510. Alternatively, the convolutional neural network 500 can comprise several convolutional layers 504, several pooling layers 506, and several fully connected layers 508, as well as other types of layers. The order of the layers can be chosen arbitrarily, usually fully connected layers 508 are used as the last layers before the output layer 510.

In particular, within a convolutional neural network 500, the nodes 512-520 of one layer 502-510 can be considered to be arranged as a d-dimensional matrix or as a d-dimensional image. In particular, in the two-dimensional case the value of the node 512-520 indexed with i and j in the n-th layer 502-510 can be denoted as $x^{(n)}_{[i,j]}$. However, the arrangement of the nodes 512-520 of one layer 502-510 does not have an effect on the calculations executed within the convolutional neural network 500 as such, since these are given solely by the structure and the weights of the edges.

In particular, a convolutional layer 504 is characterized by the structure and the weights of the incoming edges forming a convolution operation based on a certain number of kernels. In particular, the structure and the weights of the incoming edges are chosen such that the values $x^{(n)}_k$ of the nodes 514 of the convolutional layer 504 are calculated as a convolution $x^{(n)}_k = K_k * x^{(n-1)}$ based on the values $x^{(n-1)}$ of the nodes 512 of the preceding layer 502, where the convolution * is defined in the two-dimensional case as $$x^{(n)}_k[i,j] = (K_{k^*} x^{(n-1)})[i,j] = \sum_{i'}\sum_{j'} K_k[i',j'] \cdot x^{(n-1)}[i-i', j-j'].$$

Here the k-th kernel $K_k$ is a d-dimensional matrix (in this embodiment a two-dimensional matrix), which is usually small compared to the number of nodes 512-518 (e.g. a 3×3 matrix, or a 5×5 matrix). In particular, this implies that the weights of the incoming edges are not independent, but chosen such that they produce said convolution equation. In particular, for a kernel being a 3×3 matrix, there are only 9 independent weights (each entry of the kernel matrix corresponding to one independent weight), irrespectively of the number of nodes 512-520 in the respective layer 502-510. In particular, for a convolutional layer 504, the number of nodes 514 in the convolutional layer is equivalent to the number of nodes 512 in the preceding layer 502 multiplied with the number of kernels.

If the nodes 512 of the preceding layer 502 are arranged as a d-dimensional matrix, using a plurality of kernels can be interpreted as adding a further dimension (denoted as "depth" dimension), so that the nodes 514 of the convolutional layer 504 are arranged as a (d+1)-dimensional matrix. If the nodes 512 of the preceding layer 502 are already arranged as a (d+1)-dimensional matrix comprising a depth dimension, using a plurality of kernels can be interpreted as expanding along the depth dimension, so that the nodes 514 of the convolutional layer 504 are arranged also as a (d+1)-dimensional matrix, wherein the size of the (d+1)-dimensional matrix with respect to the depth dimension is by a factor of the number of kernels larger than in the preceding layer 502.

The advantage of using convolutional layers 504 is that spatially local correlation of the input data can exploited by enforcing a local connectivity pattern between nodes of adjacent layers, in particular by each node being connected to only a small region of the nodes of the preceding layer.

In embodiment shown in FIG. 5, the input layer 502 comprises 36 nodes 512, arranged as a two-dimensional 6×6 matrix. The convolutional layer 504 comprises 72 nodes 514, arranged as two two-dimensional 6×6 matrices, each of the two matrices being the result of a convolution of the values of the input layer with a kernel. Equivalently, the nodes 514 of the convolutional layer 504 can be interpreted as arranges as a three-dimensional 6×6×2 matrix, wherein the last dimension is the depth dimension.

A pooling layer 506 can be characterized by the structure and the weights of the incoming edges and the activation function of its nodes 516 forming a pooling operation based on a non-linear pooling function f. For example, in the two dimensional case the values $x^{(n)}$ of the nodes 516 of the pooling layer 506 can be calculated based on the values $x^{(n-1)}$ of the nodes 514 of the preceding layer 504 as $$x^{(n)}[i,j]=f(x^{(n-1)}[id_1,jd_2], \ldots, x^{(n-1)}[id_1+d_1-1, jd_2+d_2-1])$$

In other words, by using a pooling layer 506, the number of nodes 514, 516 can be reduced, by replacing a number d1·d2 of neighboring nodes 514 in the preceding layer 504 with a single node 516 being calculated as a function of the values of said number of neighboring nodes in the pooling layer. In particular, the pooling function f can be the max-function, the average or the L2-Norm. In particular, for a pooling layer 506 the weights of the incoming edges are fixed and are not modified by training.

The advantage of using a pooling layer 506 is that the number of nodes 514, 516 and the number of parameters is reduced. This leads to the amount of computation in the network being reduced and to a control of overfitting.

In the embodiment shown in FIG. 5, the pooling layer 506 is a max-pooling, replacing four neighboring nodes with only one node, the value being the maximum of the values of the four neighboring nodes. The max-pooling is applied to each d-dimensional matrix of the previous layer; in this embodiment, the max-pooling is applied to each of the two two-dimensional matrices, reducing the number of nodes from 72 to 18.

A fully-connected layer 508 can be characterized by the fact that a majority, in particular, all edges between nodes 516 of the previous layer 506 and the nodes 518 of the fully-connected layer 508 are present, and wherein the weight of each of the edges can be adjusted individually.

In this embodiment, the nodes 516 of the preceding layer 506 of the fully-connected layer 508 are displayed both as two-dimensional matrices, and additionally as non-related nodes (indicated as a line of nodes, wherein the number of nodes was reduced for a better presentability). In this embodiment, the number of nodes 518 in the fully connected layer 508 is equal to the number of nodes 516 in the preceding layer 506. Alternatively, the number of nodes 516, 518 can differ.

Furthermore, in this embodiment, the values of the nodes 520 of the output layer 510 are determined by applying the Softmax function onto the values of the nodes 518 of the preceding layer 508. By applying the Softmax function, the sum the values of all nodes 520 of the output layer 510 is 1, and all values of all nodes 520 of the output layer are real numbers between 0 and 1.

A convolutional neural network 500 can also comprise a ReLU (rectified linear units) layer or activation layers with non-linear transfer functions. In particular, the number of nodes and the structure of the nodes contained in a ReLU layer is equivalent to the number of nodes and the structure of the nodes contained in the preceding layer. In particular, the value of each node in the ReLU layer is calculated by applying a rectifying function to the value of the corresponding node of the preceding layer.

The input and output of different convolutional neural network blocks can be wired using summation (residual/ dense neural networks), element-wise multiplication (attention) or other differentiable operators. Therefore, the convolutional neural network architecture can be nested rather than being sequential if the whole pipeline is differentiable.

In particular, convolutional neural networks 500 can be trained based on the backpropagation algorithm. For preventing overfitting, methods of regularization can be used, e.g. dropout of nodes 512-520, stochastic pooling, use of artificial data, weight decay based on the L1 or the L2 norm, or max norm constraints. Different loss functions can be combined for training the same neural network to reflect the joint training objectives. A subset of the neural network parameters can be excluded from optimization to retain the weights pretrained on another datasets.

Systems, apparatuses, and methods described herein may be implemented using digital circuitry, or using one or more computers using well-known computer processors, memory units, storage devices, computer software, and other components. Typically, a computer includes a processor for executing instructions and one or more memories for storing instructions and data. A computer may also include, or be coupled to, one or more mass storage devices, such as one or more magnetic disks, internal hard disks and removable disks, magneto-optical disks, optical disks, etc.

Systems, apparatus, and methods described herein may be implemented using computers operating in a client-server relationship. Typically, in such a system, the client computers are located remotely from the server computer and interact via a network. The client-server relationship may be defined and controlled by computer programs running on the respective client and server computers.

Systems, apparatus, and methods described herein may be implemented within a network-based cloud computing system. In such a network-based cloud computing system, a server or another processor that is connected to a network communicates with one or more client computers via a network. A client computer may communicate with the server via a network browser application residing and operating on the client computer, for example. A client computer may store data on the server and access the data via the network. A client computer may transmit requests for data, or requests for online services, to the server via the network. The server may perform requested services and provide data to the client computer(s). The server may also transmit data adapted to cause a client computer to perform a specified function, e.g., to perform a calculation, to display specified data on a screen, etc. For example, the server may transmit a request adapted to cause a client computer to perform one or more of the steps or functions of the methods and workflows described herein, including one or more of the steps or functions of FIG. 1 or 2. Certain steps or functions of the methods and workflows described herein, including one or more of the steps or functions of FIG. 1 or 2, may be performed by a server or by another processor in a network-based cloud-computing system. Certain steps or functions of the methods and workflows described herein, including one or more of the steps of FIG. 1 or 2, may be performed by a client computer in a network-based cloud computing system. The steps or functions of the methods and workflows described herein, including one or more of the steps of FIG. 1 or 2, may be performed by a server and/or by a client computer in a network-based cloud computing system, in any combination.

Systems, apparatus, and methods described herein may be implemented using a computer program product tangibly embodied in an information carrier, e.g., in a non-transitory machine-readable storage device, for execution by a programmable processor; and the method and workflow steps described herein, including one or more of the steps or functions of FIG. 1 or 2, may be implemented using one or more computer programs that are executable by such a processor. A computer program is a set of computer program instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Figure 6:
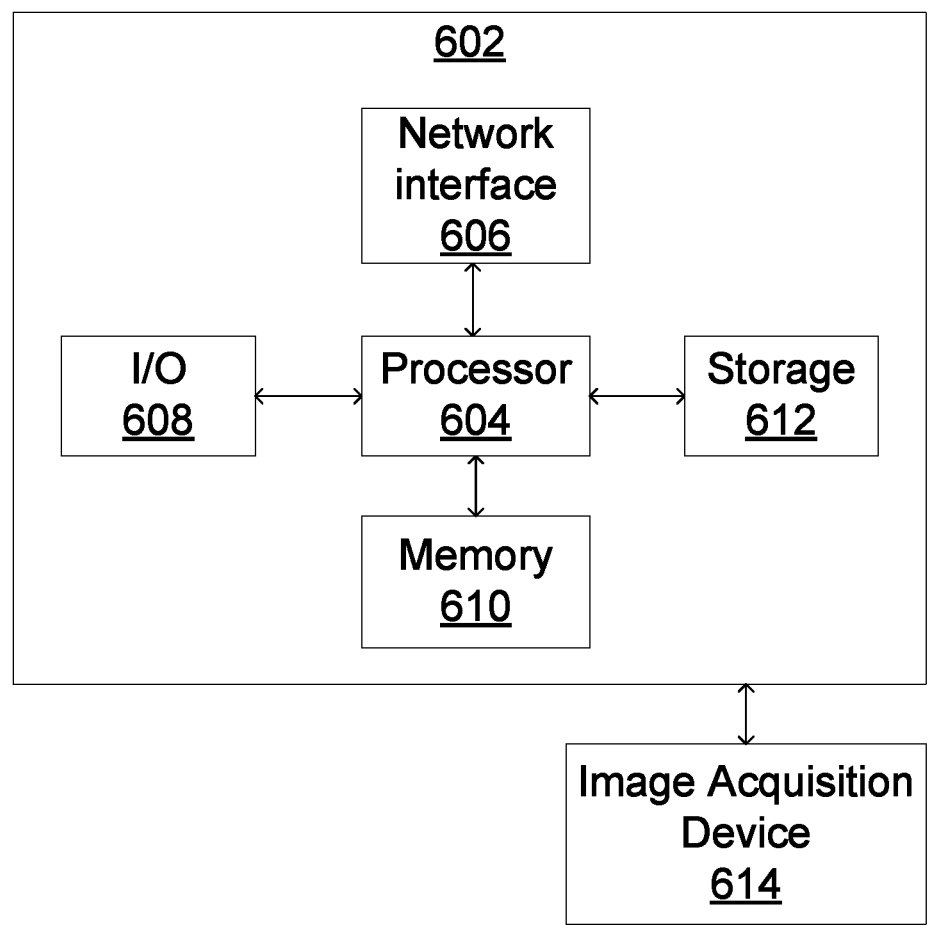
FIG. 6 shows a high-level block diagram of a computer that may be used to implement one or more embodiments.

A high-level block diagram of an example computer 602 that may be used to implement systems, apparatus, and methods described herein is depicted in FIG. 6. Computer 602 includes a processor 604 operatively coupled to a data storage device 612 and a memory 610. Processor 604 controls the overall operation of computer 602 by executing computer program instructions that define such operations. The computer program instructions may be stored in data storage device 612, or other computer readable medium, and loaded into memory 610 when execution of the computer program instructions is desired. Thus, the method and workflow steps or functions of FIG. 1 or 2 can be defined by the computer program instructions stored in memory 610 and/or data storage device 612 and controlled by processor 604 executing the computer program instructions. For example, the computer program instructions can be implemented as computer executable code programmed by one skilled in the art to perform the method and workflow steps or functions of FIG. 1 or 2. Accordingly, by executing the computer program instructions, the processor 604 executes the method and workflow steps or functions of FIG. 1 or 2. Computer 602 may also include one or more network interfaces 606 for communicating with other devices via a network. Computer 602 may also include one or more input/output devices 608 that enable user interaction with computer 602 (e.g., display, keyboard, mouse, speakers, buttons, etc.).

Processor 604 may include both general and special purpose microprocessors, and may be the sole processor or one of multiple processors of computer 602. Processor 604 may include one or more central processing units (CPUs), for example. Processor 604, data storage device 612, and/or memory 610 may include, be supplemented by, or incorporated in, one or more application-specific integrated circuits (ASICs) and/or one or more field programmable gate arrays (FPGAs).

Data storage device 612 and memory 610 each include a tangible non-transitory computer readable storage medium. Data storage device 612, and memory 610, may each include high-speed random access memory, such as dynamic random access memory (DRAM), static random access memory (SRAM), double data rate synchronous dynamic random access memory (DDR RAM), or other random access solid state memory devices, and may include non-volatile memory, such as one or more magnetic disk storage devices such as internal hard disks and removable disks, magneto-optical disk storage devices, optical disk storage devices, flash memory devices, semiconductor memory devices, such as erasable programmable read-only memory (EPROM), electrically erasable programmable read-only memory (EEPROM), compact disc read-only memory (CD-ROM), digital versatile disc read-only memory (DVD-ROM) disks, or other non-volatile solid state storage devices.

Input/output devices 608 may include peripherals, such as a printer, scanner, display screen, etc. For example, input/output devices 608 may include a display device such as a cathode ray tube (CRT) or liquid crystal display (LCD) monitor for displaying information to the user, a keyboard, and a pointing device such as a mouse or a trackball by which the user can provide input to computer 602.

An image acquisition device 614 can be connected to the computer 602 to input image data (e.g., medical images) to the computer 602. It is possible to implement the image acquisition device 614 and the computer 602 as one device. It is also possible that the image acquisition device 614 and the computer 602 communicate wirelessly through a network. In a possible embodiment, the computer 602 can be located remotely with respect to the image acquisition device 614.

Any or all of the systems and apparatus discussed herein may be implemented using one or more computers such as computer 602.

One skilled in the art will recognize that an implementation of an actual computer or computer system may have other structures and may contain other components as well, and that FIG. 6 is a high level representation of some of the components of such a computer for illustrative purposes.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A computer-implemented method comprising:
receiving an input medical image of one or more vessels in an anatomical object of a patient;
identifying one or more anatomical landmarks in the input medical image;
extracting a first patch and one or more additional patches from the input medical image based on the identified one or more anatomical landmarks, the first patch and the one or more additional patches depicting different portions of the anatomical object;
extracting features from the first patch and the one or more additional patches using a machine learning based feature extractor network, the machine learning based feature extractor network receiving as input the first patch and the one or more additional patches and generating as output the extracted features, the extracted features comprising 1) differential features comparing the first patch with each of the one or more additional patches and 2) vessel density features specific to the first patch;
detecting an occlusion in the one or more vessels in the first patch based on the extracted features; and
outputting results of the detecting.

2. The computer-implemented method of claim 1, further comprising removing bone from the input medical image and wherein extracting a first patch and one or more additional patches from the input medical image based on the identified one or more anatomical landmarks comprises:
extracting the first patch and the one or more additional patches from the bone-removed input medical image.

3. The computer-implemented method of claim 1, wherein extracting features from the first patch and the one or more additional patches using a machine learning based feature extractor network comprises:
receiving the first patch via a first input channel of the machine learning based feature extractor network and the one or more additional patches via a respective one of one or more additional input channels of the machine learning based feature extractor network.

4. The computer-implemented method of claim 1, wherein extracting a first patch and one or more additional patches from the input medical image based on the identified one or more anatomical landmarks comprises:
cropping the first patch and the one or more additional patches centered around the one or more anatomical landmarks.

5. The computer-implemented method of claim 1, wherein detecting an occlusion in the one or more vessels in the first patch based on the extracted features comprises:
detecting the occlusion in the one or more vessels in the first patch using a probability distribution function (PDF) model fitted on a set of features extracted by a neural network.

6. The computer-implemented method of claim 5, wherein the PDF model is learned using a Gaussian Process model.

7. The computer-implemented method of claim 1, wherein:
identifying one or more anatomical landmarks in the input medical image comprises identifying a middle cerebral artery (MCA) bifurcation in the input medical image;
extracting a first patch and one or more additional patches from the input medical image based on the identified one or more anatomical landmarks comprises cropping the first patch centered around the MCA bifurcation; and
detecting an occlusion in the one or more vessels in the first patch based on the extracted features comprises detecting the occlusion as being in one of an internal carotid artery (ICA), an MCA M1 segment, or MCA M2 segment.

8. The computer-implemented method of claim 1, further comprising generating at least one probability map of vessel presence for at least one of the first patch or the one or more additional patches and wherein extracting features from the first patch and the one or more additional patches using a machine learning based feature extractor network comprises:
extracting features from the at least one probability map using the machine learning based feature extractor network.

9. The computer-implemented method of claim 1, wherein the anatomical object comprises a brain of the patient and the different portions comprise a left side of the brain a right side of the brain.

10. An apparatus comprising:
means for receiving an input medical image of one or more vessels in an anatomical object of a patient;
means for identifying one or more anatomical landmarks in the input medical image;
means for extracting a first patch and one or more additional patches from the input medical image based on the identified one or more anatomical landmarks, the first patch and the one or more additional patches depicting different portions of the anatomical object;

means for extracting features from the first patch and the one or more additional patches using a machine learning based feature extractor network, the machine learning based feature extractor network receiving as input the first patch and the one or more additional patches and generating as output the extracted features, the extracted features comprising 1) differential features comparing the first patch with each of the one or more additional patches and 2) vessel density features specific to the first patch;

means for detecting an occlusion in the one or more vessels in the first patch based on the extracted features; and means for outputting results of the detecting.

11. The apparatus of claim 10, further comprising means for removing bone from the input medical image and wherein extracting a first patch and one or more additional patches from the input medical image based on the identified one or more anatomical landmarks comprises:

means for extracting the first patch and the one or more additional patches from the bone-removed input medical image.

12. The apparatus of claim 10, wherein the means for extracting features from the first patch and the one or more additional patches using a machine learning based feature extractor network comprises:

means for receiving the first patch via a first input channel of the machine learning based feature extractor network and the one or more additional patches via a respective one of one or more additional input channels of the machine learning based feature extractor network.

13. The apparatus of claim 10, wherein the means for extracting a first patch and one or more additional patches from the input medical image based on the identified one or more anatomical landmarks comprises:

means for cropping the first patch and the one or more additional patches centered around the one or more anatomical landmarks.

14. The apparatus of claim 10, wherein the anatomical object comprises a brain of the patient and the different portions comprise a left side of the brain a right side of the brain.

15. A non-transitory computer readable medium storing computer program instructions, the computer program instructions when executed by a processor cause the processor to perform operations comprising:

receiving an input medical image of one or more vessels in an anatomical object of a patient;

identifying one or more anatomical landmarks in the input medical image;

extracting a first patch and one or more additional patches from the input medical image based on the identified one or more anatomical landmarks, the first patch and the one or more additional patches depicting different portions of the anatomical object;

extracting features from the first patch and the one or more additional patches using a machine learning based feature extractor network, the machine learning based feature extractor network receiving as input the first patch and the one or more additional patches and generating as output the extracted features, the extracted features comprising 1) differential features comparing the first patch with each of the one or more additional patches and 2) vessel density features specific to the first patch;

detecting an occlusion in the one or more vessels in the first patch based on the extracted features; and outputting results of the detecting.

16. The non-transitory computer readable medium of claim 15, wherein detecting an occlusion in the one or more vessels in the first patch based on the extracted features comprises:

detecting the occlusion in the one or more vessels in the first patch using a probability distribution function (PDF) model fitted on a set of features extracted by a neural network.

17. The non-transitory computer readable medium of claim 16, wherein the PDF model is learned using a Gaussian Process model.

18. The non-transitory computer readable medium of claim 15, wherein:

identifying one or more anatomical landmarks in the input medical image comprises identifying a middle cerebral artery (MCA) bifurcation in the input medical image;

extracting a first patch and one or more additional patches from the input medical image based on the identified one or more anatomical landmarks comprises cropping the first patch centered around the MCA bifurcation; and detecting an occlusion in the one or more vessels in the first patch based on the extracted features comprises detecting the occlusion as being in one of an internal carotid artery (ICA), an MCA M1 segment, or MCA M2 segment.

19. The non-transitory computer readable medium of claim 15, the operations further comprising generating at least one probability map of vessel presence for at least one of the first patch or the one or more additional patches and wherein extracting features from the first patch and the one or more additional patches using a machine learning based feature extractor network comprises:

extracting features from the at least one probability map using the machine learning based feature extractor network.

20. The non-transitory computer readable medium of claim 15, wherein the anatomical object comprises a brain of the patient and the different portions comprise a left side of the brain a right side of the brain.

* * * * *